US010130102B2

(12) United States Patent
Bergman et al.

(10) Patent No.: US 10,130,102 B2
(45) Date of Patent: *Nov. 20, 2018

(54) DRY, FLOWABLE SABADILLA EXTRACT

(71) Applicant: McLaughlin Gormley King Company, Golden Valley, MN (US)

(72) Inventors: John Thomas Bergman, Saint Louis Park, MN (US); Darrick David Unger, Minnetonka, MN (US)

(73) Assignee: MCLAUGHLIN GORMLEY KING COMPANY, Golden Valley, MN (US)

( * ) Notice: Subject to any disclaimer, the term of this patent is extended or adjusted under 35 U.S.C. 154(b) by 286 days.

This patent is subject to a terminal disclaimer.

(21) Appl. No.: 15/299,835

(22) Filed: Oct. 21, 2016

(65) Prior Publication Data

US 2017/0112140 A1 Apr. 27, 2017

Related U.S. Application Data

(60) Provisional application No. 62/244,891, filed on Oct. 22, 2015.

(51) Int. Cl.
*A61K 36/00* (2006.01)
*A01N 65/40* (2009.01)
*A01N 25/12* (2006.01)
*A01N 65/42* (2009.01)

(52) U.S. Cl.
CPC ............. *A01N 65/40* (2013.01); *A01N 25/12* (2013.01); *A01N 65/42* (2013.01)

(58) Field of Classification Search
CPC ...................................................... A61K 36/00
USPC .......................................................... 424/725
See application file for complete search history.

(56) References Cited

U.S. PATENT DOCUMENTS

| 2,348,949 | A | 5/1944 | Allen et al. |
| 2,390,911 | A | 12/1945 | Allen et al. |
| 3,078,211 | A * | 2/1963 | Allison .................. A01N 43/90 424/753 |
| 6,254,864 | B1 | 7/2001 | Stimac et al. |
| 6,309,678 | B1 | 10/2001 | Kahol et al. |
| 2015/0157027 | A1 | 6/2015 | Harman |
| 2015/0216181 | A1 | 8/2015 | Hernandez et al. |

OTHER PUBLICATIONS

International Search Report and Written Opinion issued by the International Bureau in corresponding application No. PCT/US2016/058065 dated Jan. 17, 2017.

* cited by examiner

*Primary Examiner* — Michael V Meller
(74) *Attorney, Agent, or Firm* — Wood, Phillips, Katz, Clark & Mortimer

(57) ABSTRACT

The invention relates to methods for preparing a dry, flowable sabadilla extract and to methods of its use as a pesticide.

1 Claim, No Drawings

DRY, FLOWABLE SABADILLA EXTRACT

FIELD OF THE INVENTION

The present invention is directed to methods of preparing a dry, flowable sabadilla extract and methods of its use as a pesticide.

BACKGROUND OF THE INVENTION

Controlling damaging pests on plants grown to provide human food is a constant struggle for growers. Insects can completely destroy a harvest and can cause catastrophic food shortages or financial ruin for the growers. Although many products are effective against insects that damage plants, the products must also be safe enough to be released into the growing environment and safe enough to be applied to parts of the plants that will eventually be consumed.

Organic farming is increasing in popularity. Organic farming restricts the use of compounds that are used for pest control to encourage sustainability and safety. Insecticides can be used in organic farming if they are considered "natural." Unfortunately, many of the natural insecticides currently available are not potent enough to provide adequate insect control. Further, many of the currently available natural pesticides are not practical to apply or their application is cost prohibitive.

One effective naturally derived insecticide is found in the tissues of many of the plants of the genus *Schoenocaulon*, commonly referred to as sabadilla. The species with the longest history of use, and the most readily available, is *Schoenocaulon officinale*. The plant is indigenous to Central and South America and its seeds have been used for centuries for their insecticidal properties. The seeds contain the alkaloids veratridine and cevadine, both of which are known to be active against arthropods.

Usually the dried seeds are ground to a powder and the powder is applied dry or wetted to the insects or their environment. The seeds must be milled into smaller particles in order to be applied to the insects. The milling process usually requires an oil absorbing adjuvant to prevent the seeds from caking. This adjuvant dilutes the alkaloids in the ground seeds. Also, the ground seeds can be difficult to apply to areas in need of treatment because the seed particles and anti-caking adjuvant can clog spraying equipment. Another disadvantage of using ground seeds is that the dust from the seeds can cause eye and nasal irritation. Further, the ground seed powder is often not potent enough to control large infestations.

U.S. Pat. Nos. 2,348,949 and 2,390,911 disclose the use of ground sabadilla seeds with beta-butoxy-beta-prime-thiocyanodiethyl-ether to control houseflies. Further, these patents teach heating the seeds and using them as a powder, or mixing them with kerosene to form a sprayable formulation. Neither of these disclosed mixtures of ground sabadilla seeds would be appropriate for organic farming.

Accordingly, there is a need for new methods of controlling insects. The methods should be potent, safe for growers to apply, safe to beneficial organisms (target specific), and safe for the environment.

SUMMARY OF THE INVENTION

In one aspect, the present invention is directed to methods for creating a dry, flowable sabadilla extract.

In another aspect, the present invention is directed to methods for controlling pests comprising applying a dry, flowable sabadilla extract to pests or to their environment.

In a further aspect, the present invention is directed to a pesticidal sabadilla extract product produced by the process comprising the steps of milling sabadilla seeds or other plant parts, washing the milled sabadilla seeds or other plant parts with at least one seed or plant part extract selected from the group consisting of methanol, ethanol, glycol ether, ethyl lactate, propanol, butyl lactate, gamma-butyrolactone, and 1-butanol under agitation to dissolve the sabadilla extract in the seed or plant part solvent, removing the sabadilla extract in the seed or plant part solvent from the washed milled seeds or other plant parts, adding a drying agent selected from the group consisting of manufactured silica, diatomaceous earth, and maltodextrin to the sabadilla extract, and removing the seed or plant part solvent to produce the dry, flowable pesticidal sabadilla extract.

In a preferred embodiment the sabadilla extract is prepared from sabadilla seeds.

DETAILED DESCRIPTION OF THE INVENTION

Applicant has unexpectedly developed new methods for producing a dry, flowable sabadilla extract. While sabadilla extracts are desirable because they can concentrate the alkaloids, they can also be very difficult to handle and have a tar-like viscosity. Applicant unexpectedly developed a way to make the sabadilla extract easy to handle, use and apply.

One method that Applicant developed involves creating an extract of sabadilla seeds or other plant parts by removing the solid inert parts, such as the cellulose, hemicellulose, lignin and pectin, from the rest of the material with seed or plant part solvent. A drying agent is then added to the extract.

An alternative method involves creating an extract by removing the oil and the solid inert parts from the whole seeds or other plant parts, and then adding a drying agent to the extract. The oil can be removed first or the solid inert parts can be removed first.

Both methods produce a dry, flowable extract that contains the alkaloids in a more concentrated form. The concentrated dry, flowable sabadilla extract is more effective than the ground whole seeds or other plant parts because the parts that do not contain alkaloids have been removed from the extract.

Further, the inert parts of the seeds or other plant parts can no longer clog spray equipment. Yet another advantage of the concentrated sabadilla extract is that it is easier to handle and can be formulated in various user-friendly products to meet the needs of growers. Applicant's methods for production of the concentrated sabadilla extract are also high yielding and can be easily scaled up for commercial use.

In one embodiment, the present invention is directed to methods for producing a dry, flowable pesticidal sabadilla extract comprising milling sabadilla seeds or other plant parts, washing the milled sabadilla seeds or other plant parts with at least one seed or plant part extract selected from the group consisting of methanol, ethanol, glycol ether, ethyl lactate, propanol, butyl lactate, gamma-butyrolactone, and 1-butanol under agitation to dissolve the sabadilla extract in the seed or plant part solvent, removing the sabadilla extract in the seed or plant part solvent from the washed milled seeds or other plant parts, adding a drying agent selected from the group consisting of manufactured silica, diatomaceous earth, and maltodextrin to the sabadilla extract, and removing seed or plant part solvent to produce a dry, flowable pesticidal sabadilla extract. In all embodiments, the solid, friable material left once all of the seed or plant part extract is removed is easily reduced to a powder.

Sabadilla seeds and extract may be derived from any species of *Schoenocaulon*. The genus *Schoenocaulon* includes the following species: *Schoenocaulon calcicola, Schoenocaulon caricifolium, Schoenocaulon comatum, Schoenocaulon conzattii, Schoenocaulon dubium* (alt. *Schoenocaulon gracile*), *Schoenocaulon framei, Schoenocaulon ghiesbreghtii* (alt. *Schoenocaulon drummondii, Schoenocaulon yucatanense*), *Schoenocaulon ignigenum, Schoenocaulon intermedium, Schoenocaulon jaliscense, Schoenocaulon macrocarpum* (alt. *Schoenocaulon lauricola*), *Schoenocaulon madidorum, Schoenocaulon megarrhizum, Schoenocaulon mortonii, Schoenocaulon oaxacense, Schoenocaulon obtusum, Schoenocaulon officinale, Schoenocaulon pellucidum, Schoenocaulon plumosum, Schoenocaulon pringlei, Schoenocaulon rzedowskii, Schoenocaulon tenorioi, Schoenocaulon tenue, Schoenocaulon tenuifolium, Schoenocaulon texanum*, and *Schoenocaulon tigrense*.

In a preferred embodiment, the sabadilla seeds and extract are derived from *S. officinale*.

To optimize solvent penetration and subsequent extraction, the seed coat must be ruptured and the distance between penetrable surfaces of the seed reduced as much as possible. The can be achieved by milling the seeds.

Sabadilla seeds are very difficult to cleanly break into fine pieces. The bulk of the seed is hard and oily and requires a lot of energy to pulverize, producing heat due to high friction. Any suitable milling method can be used. Applicant found that cryogenic hammer milling the seeds was ideal for efficient extraction of the sabadilla oil.

Cryogenic grinding, or cryomilling, most commonly uses dry ice, liquid carbon dioxide or liquid nitrogen to cool the feed material in a mill of an otherwise conventional design (e.g. a cryogenic hammermill.) This super-cooling makes the sabadilla seed more uniformly brittle, in turn making it easier to control particle size. Additionally, the oil in the seed is a solid at the temperature of liquid nitrogen, and does not slow processing speed. This increased friability and solidification of the oil allows for very efficient throughput rates during milling.

Flake milling, most commonly using a roller-type mill, was found to create a milled sabadilla seed that was somewhat more efficient to handle during processing than cryogenically hammer milled seed, but allowed a less efficient extraction. In a flake milling procedure, the seeds are heated to increase plasticity and passed between rollers which flatten the seeds into thin, solvent-penetrable flakes that are still largely one piece. Flaking usually produces a minimal amount of fine particles which hinder efficient processing.

Pin milling may also be used but this technique produces particles which are coarse and require more time to process than other milling products. Conventional, ambient, hammer milling and "Fitz" milling may also be used to produce a sufficiently sized particle, however, throughput rates are generally inefficient and it is difficult to control particle size.

While flake milling's larger particle size overall makes it simplest and easiest to handle during processing, Applicant found that cryogenic hammer milling allowed the creation of sabadilla seed particles over a range of sizes that enable a more efficient extraction of sabadilla oil with only a modest increase in material handling difficulty. Accordingly, Applicant found that cryogenic hammer milling with liquid nitrogen was a superior milling approach for producing sabadilla oil.

The sabadilla seeds or sabadilla extract can be washed with at least one extract solvent selected from the group consisting of C5 to C14 alkanes, chlorinated methane, chlorinated ethane, benzene, and benzene derivatives one time or multiple times. For example, the sabadilla seeds can be washed one to ten times. Applicant found that more than half of the oil can be extracted from the milled seeds with a single wash. If the extract solvent is decanted and additional extract solvent added (additional washes), then the yield is increased. Applicant found that 5 washes could successfully remove 100% of the oil from the milled sabadilla seeds. For example, if 500 grams of milled seeds were washed 5 times with a total of 2.5 kilograms of hexane, 100% of the oil was removed from the milled sabadilla seeds. This is a 1:5 weight ratio of milled seed to extract solvent. This ratio can be used to scale up the production to a commercial scale. In an embodiment, the milled sabadilla seeds are washed with at least one extract solvent selected from the group consisting of C5 to C14 alkanes, chlorinated methane, chlorinated ethane, benzene, and benzene derivatives from 1 to 5 times. In a preferred embodiment, the milled sabadilla seeds are washed with the extract solvent from 2 to 5 times. In a most preferred embodiment, the milled sabadilla seeds are washed with the extract solvent 5 times.

The sabadilla extract can be washed with the extract solvent one time or multiple times. For example, the sabadilla extract can be washed one to ten times.

During the extraction, the milled sabadilla seeds and extract solvent should be agitated. This can be done by any method known by those of skill in the art. Applicant found that stirring the milled sabadilla seeds in the extract solvent increased the rate of extraction and was an effective means of agitation. The process was most efficient if the stirring was brisk enough to prevent the milled sabadilla seeds from settling in the extraction/washing vessel (e.g., flask).

During the extraction, the sabadilla extract and extract solvent should be agitated. This can be done by any method known by those of skill in the art. The process was most efficient if the stirring was brisk enough to prevent the sediment from the sabadilla extract from settling in the extraction/washing vessel (e.g., flask).

As used herein, the "seed or plant part solvent" refers to methanol, ethanol, glycol ether, ethyl lactate, propanol, butyl lactate, gamma-butyrolactone, and/or 1-butanol.

In a preferred embodiment, the seeds or plant part solvent is selected from the group consisting of methanol, ethanol, glycol ether, ethyl lactate, and propanol. In a more preferred embodiment, the seed or plant part solvent is methanol.

Methanol can be used at temperatures from about 0 to about 60 degrees Celsius. Applicant found that methanol at lower temperatures required additional extraction time and that temperatures above about 55 to 60 degrees Celsius resulted in methanol loss and boiling. Applicant found that the optimal temperature for methanol extraction was from about 50 to about 55 degrees Celsius.

In another embodiment, the sabadilla extract is washed with at least one extract solvent selected from the group consisting of C5 to C14 alkanes, chlorinated methane, chlorinated ethane, benzene, and benzene derivatives.

In a further embodiment, the milled sabadilla seeds are washed at least one extract solvent selected from the group consisting of C5 to C14 alkanes, chlorinated methane, chlorinated ethane, benzene, and benzene derivatives before they are washed with the seed or plant part solvent.

The milled sabadilla seeds or sabadilla extract can be washed with at least one extract solvent selected from the group consisting of C5 to C14 alkanes, chlorinated methane, chlorinated ethane, benzene, and benzene derivatives one time or multiple times. For example, the milled sabadilla seeds or sabadilla extract can be washed one to ten times. If the at least one extract solvent selected from the group consisting of C5 to C14 alkanes, chlorinated methane, chlorinated ethane, benzene, and benzene derivatives is decanted and additional solvent is added (additional washes), then the purity of the extract is increased.

In an embodiment, the milled sabadilla seeds or sabadilla extract are washed with at least one extract solvent selected from the group consisting of C5 to C14 alkanes, chlorinated methane, chlorinated ethane, benzene, and benzene derivatives from 1 to 5 times. In a preferred embodiment, the milled sabadilla seeds or sabadilla extract are washed with at least one extract solvent selected from the group consisting of C5 to C14 alkanes, chlorinated methane, chlorinated ethane, benzene, and benzene derivatives from 2 to 5 times. In a most preferred embodiment, the milled sabadilla seeds or sabadilla extract are washed with at least one extract solvent selected from the group consisting of C5 to C14 alkanes, chlorinated methane, chlorinated ethane, benzene, and benzene derivatives 5 times.

During the washes, the milled sabadilla seeds or sabadilla extract and at least one extract solvent selected from the group consisting of C5 to C14 alkanes, chlorinated methane, chlorinated ethane, benzene, and benzene derivatives should be agitated. This can be done by any method known by those of skill in the art. Applicant found that stirring the milled sabadilla seeds or sabadilla extract in the at least one extract solvent selected from the group consisting of C5 to C14 alkanes, chlorinated methane, chlorinated ethane, benzene, and benzene derivatives increased the rate of extraction and was an effective means of agitation.

In an embodiment, the at least one extract solvent selected from the group consisting of C5 to C14 alkanes, chlorinated methane, chlorinated ethane, benzene, and benzene derivatives is removed from the extract by evaporation, including distillation.

In a preferred embodiment, the at least one extract solvent selected from the group consisting of C5 to C14 alkanes, chlorinated methane, chlorinated ethane, benzene, and benzene derivatives is hexane. Hexane can be used at temperatures from about 0 to about 50 degrees Celsius. Applicant found that hexane at lower temperatures required additional extraction time and that temperatures above about 45 to about 50 degrees Celsius resulted in hexane loss and boiling. Applicant found that the optimal temperature for hexane extraction was from about 40 to about 45 degrees Celsius.

In an embodiment, the washed milled seeds are separated from the at least one extract solvent selected from the group consisting of C5 to C14 alkanes, chlorinated methane, chlorinated ethane, benzene, and benzene derivatives by decanting (pouring), pumping, or draining. For example, when the extract is produced on a small scale, the milled seeds settle to the bottom of the flask and the extract solvent can be easily decanted out of the flask. During commercial extraction production, the extract solvent can be removed by methods known by those of skill in the art. For example, the extract solvent could be removed from the washing vessel by draining the extract solvent with the use of a screen, pump, or filter.

In another embodiment, sabadilla oil can be extracted from milled sabadilla seeds using countercurrent extraction. Countercurrent extraction is a commercial scale extraction process typically used in oil seed extraction of seeds such as canola and soy. In brief, countercurrent extraction is a continuous process in which fresh, milled seed is fed through a long solvent bath by conveyor. The seed enters one end and the solvent enters the other, both eventually exiting opposite ends of the apparatus as spent marc (i.e. extracted/depleted seed) and miscella (i.e. solvent with a solute load from the seed).

In a preferred embodiment, the drying agent is manufactured silica. "Manufactured silica" refers to silica that has been processed to create fine particles. Preferably the particles have an average particle size (d50) of from about 5 to about 50 microns. More preferably the particles have an average particle size of from about 8 to about 15.

Applicant found that manufactured silica was desirable as it did not impact the pH of the concentrated extract, could be used at lower ratios of addition than other products (reducing dilution of the seed concentrate), and created a stable, easy to handle product. Zeofree® 80 (Zeofree is a registered trademark of and available from J. M. Huber Corporation) is one presently preferred product.

In an embodiment, the weight ratio of manufactured silica to sabadilla extract is from about 1:15 to about 1:0.05. In a preferred embodiment, the weight ratio of manufactured silica to sabadilla seed extract is from about 1:8 to about 1:1. In a more preferred embodiment, the weight ratio of manufactured silica to sabadilla extract is from about 1:4 to about 1:2.

In an embodiment, the drying agent is diatomaceous earth. In a preferred embodiment, the weight ratio of diatomaceous earth to sabadilla extract is from about 1:10 to about 1:0.05. In a more preferred embodiment, the weight ratio of diatomaceous earth to sabadilla extract is from about 1:5 to about 1:0.25. In a most preferred embodiment, the weight ratio of diatomaceous earth to sabadilla extract is from about 1:2 to about 1:0.5.

In yet another embodiment, the drying agent is maltodextrin and at least one extract solvent selected from the group consisting of C5 to C14 alkanes, chlorinated methane, chlorinated ethane, benzene, and benzene derivatives is used to wash the milled seeds before the seed or plant part solvent washes. In a preferred embodiment, the weight ratio of maltodextrin to sabadilla extract is from about 1:4 to about 1:50. In a more preferred embodiment, the weight ratio of maltodextrin to sabadilla extract is from about 1:10 to about 1:40. In a most preferred embodiment, the weight ratio of maltodextrin to sabadilla extract is from about 1:15 to about 1:35.

In a further embodiment, the drying agent is maltodextrin and at least one extract solvent selected from the group consisting of C5 to C14 alkanes, chlorinated methane, chlorinated ethane, benzene, and benzene derivatives is used to wash the sabadilla extract. In a preferred embodiment, the weight ratio of maltodextrin to sabadilla extract is from about 1:4 to about 1:50. In a more preferred embodiment, the weight ratio of maltodextrin to sabadilla seed extract is from about 1:10 to about 1:40. In a most preferred embodiment, the weight ratio of maltodextrin to sabadilla extract is from about 1:15 to about 1:35.

In another embodiment, the present invention is directed to methods for controlling insects comprising applying the dry, flowable sabadilla extract produced by the methods of the present invention to pests or the pests' environment.

In another embodiment, the pests controlled are selected from the group consisting of members of the class Insecta (insects), Arachnida subclass Acari (mites), and shell-less terrestrial gastropod mollusks (slugs).

In an embodiment, the insects controlled are selected from the group consisting of aphids (Hemiptera), whiteflies (Hemiptera), thrips (Thysanoptera), leafhoppers (Hemiptera), bed bugs (Hemiptera), psyllids (Hemiptera), scale insects (Hemiptera), mealybugs (Hemiptera), psocids (Psocoptera), lice (Phthiraptera), fleas (Siphonaptera), caterpillars (Lepidoptera), and early immature stages of beetles (Coleoptera), true bugs (Hemiptera), cockroaches (Blattodea), flies (Diptera) and wasps (Hymenoptera). In a preferred embodiment, the insects controlled are selected from the group consisting of aphids (Hemiptera), whiteflies (Hemiptera), thrips (Thysanoptera), leafhoppers (Hemiptera), bed bugs (Hemiptera), psyllids (Hemiptera), scale insects (Hemiptera), mealybugs (Hemiptera), psocids (Psocoptera), lice (Phthiraptera), and fleas (Siphonaptera). In a more preferred embodiment, the insects controlled are selected from the group consisting of bed bugs (*Cimex lectularius*), western flower thrips (*Frankliniella occidentalis*), green peach aphids (*Myzus persicae*), and greenhouse whitefly (*Trialeurodes vaporariorum*).

In a preferred embodiment, the mites controlled are two-spotted spider mites (*Tetranychus urticae*).

The dry, flowable pesticidal sabadilla extract is a contact pesticide which means that the extract should be applied directly to the pests or their environment for the most effective control. The extract, or a formulation containing the extract, can be mixed with water and applied with a pressurized system, such as aerosol generators or in a form of ground application, e.g., low pressure boom sprayers, high pressure sprayers, air blast sprayers, low volume air sprayers (mist blowers), hand-operated sprayers and pump sprays. The extract should be applied as a fine spray until the surface is uniformly wet with minimal runoff. In another embodiment, the extract can be formulated, for example, as granules, and applied by broadcast.

In yet another embodiment, the present invention is directed to a dry, flowable pesticidal sabadilla extract product produced by the process comprising the steps of milling sabadilla seeds, washing the milled sabadilla seeds with at least one seed or plant part extract selected from the group consisting of methanol, ethanol, glycol ether, ethyl lactate, propanol, butyl lactate, gamma-butyrolactone, and 1-butanol under agitation to dissolve the sabadilla extract in the seed or plant part solvent, removing the sabadilla extract in the seed or plant part solvent from the washed milled seeds, adding a drying agent selected from the group consisting of manufactured silica, diatomaceous earth, and maltodextrin to the sabadilla extract, and removing the seed or plant part solvent to produce the dry, flowable pesticidal sabadilla extract.

In a preferred embodiment, the sabadilla seeds are sabadilla seeds which can be derived from *S. officinale* plant.

In an embodiment, the milled sabadilla seeds or the sabadilla extract are washed with at least one extract solvent selected from the group consisting of C5 to C14 alkanes, chlorinated methane, chlorinated ethane, benzene, and benzene derivatives and the extract solvent and oil are then removed from the extract.

As used herein, "extract solvent" refers to C5 to C14 alkanes, chlorinated methane, chlorinated ethane, benzene, and/or benzene derivatives. As used herein, "benzene derivatives" refers to a chemical compound derived from benzene wherein one or more hydrogen atoms are replaced with another functional group. Examples of benzene derivatives include phenol, toluene, and aniline.

In a further embodiment, the seed or plant part solvent is partially removed from the washed milled seeds before the drying agent is added.

As used herein, "dry, flowable sabadilla extract" refers to an extract of sabadilla seeds or other plant parts which is substantially free of cellulose, hemicellulose, lignin, and pectin and includes a drying agent. The dry, flowable sabadilla extract may or may not contain sabadilla oils.

As used herein, "sabadilla extract" refers to an extract of sabadilla seeds or other plant parts which has had a part of the seed or other plant parts removed in order to concentrate the alkaloids.

The dry, flowable sabadilla extract of the present invention is distinct from sabadilla seeds in their natural state because the extract has been isolated from the seed, concentrated, and a drying agent has been added. The sabadilla extract of the present invention is not present in nature in this form.

As used herein, "controlling pests" refers to decreasing the negative impact of pests on plants or animals to a level that is desirable to the grower or animal.

As used herein, "roller mill" refers to equipment used to decrease the shape of a material by pressing the material with at least one cylindrical roller against another roller or firm surface. A roller mill is one way of producing a flaked seed.

As used herein, "pests' environment" refers to any area that the pest is present during any life stage. One environment likely to be treated by the methods of the present invention includes the plants that the pests are living on and the surrounding soil. The pests' environment may include soil, plants, harvested plants, gardens, fields, greenhouses, or other buildings, and various indoor surfaces and structures, such as furniture including beds, and furnishings including books, clothing, etc.

As used herein, all numerical values relating to amounts, weight percentages and the like are defined as "about" or "approximately" each particular value, namely, plus or minus 10% (±10%). For example, the phrase "at least 5% by weight" is to be understood as "at least 4.5% to 5.5% by weight." Therefore, amounts within 10% of the claimed values are encompassed by the scope of the claims.

The articles "a," "an" and "the" are intended to include the plural as well as the singular, unless the context clearly indicates otherwise. For example, the methods of the present invention are directed to controlling "pests" but this can include control of a single pest (such as a single insect).

The following examples are intended to illustrate the present invention and to teach one of ordinary skill in the art how to use the extracts of the invention. They are not intended to be limiting in any way.

EXAMPLES

Example 1

Sabadilla seeds were flake milled according to the manufacturer's instructions. Two hundred grams of milled seed were added to a three liter flask with methanol and stirred with a three blade stirrer controlled by an overhead motor. A stirring speed was maintained which prevented any seed fragments from settling in the flask. The system was sealed to limit evaporation loss.

The methanol dissolves the sabadilla seed extract but does not dissolve the solid inert parts of the seeds, such as cellulose. The methanol and dissolved sabadilla seed extract were decanted off and additional methanol was added to the flask. This step was repeated three additional times. The washed milled seeds remained in the bottom of the flask when the methanol and dissolved sabadilla extract were decanted.

The methanol and dissolved sabadilla extract were placed in a new flask. Distillation was then used to remove the methanol from the methanol and dissolved sabadilla seed extract solution. Standard IKA rotary evaporators were used for the distillation. The flask containing the methanol and dissolved sabadilla extract solution was loaded into the evaporator and into a heated water bath. The flask was heated to between 50 to 55 degrees Celsius at below atmospheric pressure in order to maximize efficient removal of the methanol without allowing it to boil over into the condenser. The evaporated methanol was partially condensed in an adjoining flask leaving some methanol in the concentrated sabadilla extract solution.

Then, 12.5 grams of manufactured silica was added to the flask containing the concentrated sabadilla extract with some methanol. The distillation was then continued until the methanol was gone.

Accordingly, an easy to handle, dry, flowable sabadilla extract was prepared.

Example 2

The same procedure as explained in Example 1 was used except that 35 grams of diatomaceous earth was added instead of manufactured silica to the partially distilled methanol and concentrated sabadilla seed extract solution. Accordingly, a dry, flowable sabadilla extract was prepared using a different drying agent.

Example 3

Sabadilla seeds were flake milled according to the manufacturer's instructions. Two hundred grams of milled seed were added to a three liter flask with hexane and stirred with a three blade stirrer controlled by an overhead motor. This step removes the oil from the seeds. A stirring speed was maintained which prevented any seed fragments from settling in the flask. The system was sealed to limit evaporation loss.

The hexane and dissolved oil were decanted off and additional hexane was added to the flask. This step was repeated three additional times. The washed milled seeds (now de-oiled) remained in the flask when the hexane and dissolved oil were decanted off. The hexane and dissolved oil can be discarded or used for another purpose.

The de-oiled washed milled seeds in the flask were then washed with methanol to remove the solid seed parts from the extract. The methanol and dissolved extract was decanted off and additional methanol was added to the flask. This step was repeated three additional times. The washed milled seeds remained in the bottom of the flask when the methanol and dissolved extract were decanted.

The decanted methanol with dissolved extract were placed in a new flask. Distillation was then used to separate the methanol from the methanol and dissolved extract. Standard IKA rotary evaporators were used for the distillation. The flask containing the methanol and dissolved extract was loaded into the evaporator and into a heated water bath. The flask was heated to between 50 to 55 degrees Celsius in order to maximize efficient removal of the methanol without allowing it to boil over into the condenser. The evaporated methanol was partially condensed in an adjoining flask leaving some of the methanol in the concentrated sabadilla seed extract solution.

Then, 1.6 grams of maltodextrin was added to the flask containing the concentrated extract with some methanol. The distillation was then continued until the methanol was gone.

Accordingly, an easy to handle, dry, flowable sabadilla seed extract was prepared.

Example 4

Sabadilla seeds were flake milled according to the manufacturer's instructions. Two hundred grams of milled seed were added to a three liter flask with methanol and stirred with a three blade stirrer controlled by an overhead motor. This step separates the solid seed parts, such as cellulose, from the seeds. A stirring speed was maintained which prevented any seed fragments from settling in the flask. The system was sealed to limit evaporation loss.

The methanol dissolves the sabadilla extract but does not dissolve the solid inert parts of the seeds, such as cellulose. The methanol and dissolved sabadilla extract were decanted off and additional methanol was added to the flask. This step was repeated three additional times. The washed milled seeds remained in the bottom of the flask when the methanol and dissolved sabadilla extract were decanted.

The methanol and dissolved sabadilla extract were placed in a new flask. Distillation was then used to remove the methanol from the methanol and dissolved sabadilla extract solution. Standard IKA rotary evaporators were used for the distillation. The flask containing the methanol and dissolved sabadilla extract solution was loaded into the evaporator and into a heated water bath. The flask was heated to between 50 to 55 degrees Celsius at below atmospheric pressure in order to maximize efficient removal of the methanol without allowing it to boil over into the condenser. The evaporated methanol was thoroughly condensed in an adjoining flask leaving the concentrated sabadilla extract solution.

The concentrated sabadilla extract solution was then washed with hexane to remove the oil. The hexane and dissolved oil were decanted off and additional hexane was added to the flask. This step was repeated three additional times. The hexane and dissolved oil can be discarded or used for another purpose.

The de-oiled sabadilla extract remained in the flask. Then, 1.6 grams of maltodextrin was added to the flask containing the concentrated extract and stirred in.

Accordingly, an easy to handle, dry, flowable sabadilla extract was prepared.

We claim:

1. A pesticidal sabadilla extract produced by the process consisting essentially of the steps of: milling sabadilla seeds;
    washing the milled sabadilla seeds with at least one solvent selected from the group consisting of glycol ether, ethyl lactate, propanol, butyl lactate, gamma-butyrolactone, and 1-butanol under agitation to dissolve the sabadilla extract in the solvent;
    removing the sabadilla extract in the solvent from the washed milled seeds;
    adding manufactured silica and maltodextrin to the sabadilla extract; and
    removing the solvent to produce the pesticidal sabadilla extract.

* * * * *